United States Patent [19]
Harris et al.

[11] Patent Number: 6,040,482
[45] Date of Patent: Mar. 21, 2000

[54] OXYALKYLENE-SUBSTITUTED AMINOPHENOL INTERMEDIATE

[75] Inventors: Philip G. Harris; Rajnish Batlaw, both of Spartanburg, S.C.

[73] Assignee: Milliken & Company, Spartanburg, S.C.

[21] Appl. No.: 09/263,902

[22] Filed: Mar. 5, 1999

[51] Int. Cl.$^7$ .................. C07C 215/00; C07C 211/00
[52] U.S. Cl. ............................ 564/443; 564/442
[58] Field of Search ...................... 564/443, 442

[56] References Cited

U.S. PATENT DOCUMENTS

| | | | |
|---|---|---|---|
| 4,806,657 | 2/1989 | Zink | 549/226 |
| 5,250,708 | 10/1993 | Barry, Jr. | 549/226 |

FOREIGN PATENT DOCUMENTS 0 468 821 A1   1/1992   European Pat. Off. .

*Primary Examiner*—Paul J. Killos
*Attorney, Agent, or Firm*—Terry T. Moyer; William S. Parks

[57] ABSTRACT

This invention relates to very specific oxyalkylene-substituted aminophenol compounds as intermediates for the production of poly(oxyalkylene)-substituted xanthene (or other type) colorants. Such an inventive intermediate compound is produced in a single step by reacting an oxyalkylene oxide having from 3 to 12 carbon atoms (branched or unbranched), glycidol, or a glycidyl directly with aminophenol without the use of a catalyst and at a relatively low temperature. Propylene oxide and m-aminophenol are the preferred reactants. The propylene oxide selectively reacts with the amine group on the m-aminophenol without propoxylating the phenolic hydroxyl group. Such a specific method thus does not require extra time- and cost-consuming steps of protecting the phenolic hydroxyl group from attack. After production, this intermediate may be reacted with suitable compounds to ultimately form any number of different colorants, including xanthenes, oxazines, coumarins, and the like. The resultant oxypropylene groups may subsequently be reacted with electrophile compounds to produce any number of different colorants. Resultant colorants produced through the reaction of the inventive intermediate are also contemplated within this invention.

15 Claims, No Drawings

OXYALKYLENE-SUBSTITUTED AMINOPHENOL INTERMEDIATE

FIELD OF THE INVENTION

This invention relates to very specific oxyalkylene-substituted aminophenol compounds as intermediates for the production of poly(oxyalkylene)-substituted xanthene (or other type) colorants. Such an inventive intermediate compound is produced in a single step by reacting an oxyalkylene oxide or oxyalkylester having from 3 to 12 carbon atoms (branched or unbranched), glycidol, or a glycidyl directly with aminophenol without the use of a catalyst and at a relatively low temperature. Propylene oxide and m-aminophenol are the preferred reactants. The propylene oxide selectively reacts with the amine group on the m-aminophenol without propoxylating the phenolic hydroxyl group. Such a specific method thus does not require extra time- and cost-consuming steps of protecting the phenolic hydroxyl group from attack. After production, this intermediate may be reacted with suitable compounds to ultimately form any number of different colorants, including xanthenes, oxazines, coumarins, and the like. The resultant oxypropylene groups may subsequently be reacted with electrophile compounds to produce any number of different colorants. Resultant colorants produced through the reaction of the inventive intermediate are also contemplated within this invention.

DISCUSSION OF THE PRIOR ART

All U.S. and foreign patents cited within this specification are hereby incorporated by reference. Xanthene colorants provide red, bluish red, and magenta tints within the colorant industry. However, the versatility of such colorants within and on different substrates had proven difficult to accomplish in the past. It was believed that the ability to potentially increase the number of available substrates for which such colorants could be used was possible upon the addition of oxyalkylene groups to the colorant itself. Such a reaction is not possible with the already formed xanthene system. However, it was theorized that the formation of an oxyalkylenated aminophenol intermediate could provide the desired effect upon production of the xanthene from the intermediate. Such an intermediate was first produced in U.S. Pat. No. 5,250,708 to Barry, Jr. and provided the ability of producing such desirable xanthene derivative colorants.

Thus, poly(oxyalkylenated) xanthene colorants have only recently been made available to the colorant market. However, even with the intermediate provided by the '708 patent, the limiting factor in producing such colorants has still proven to be the cost- and time-effective formation of a poly(oxyalkylenated) aminophenol intermediate which would subsequently react with phthalic anhydride to form the desired poly(oxyalkylenated) xanthene derivative compound. Patentee formed the intermediate, which required at least 6 moles of alkylene oxide to be reacted to form the desired oxyalkylenated intermediate, through a five-step process which included the protection of the phenolic hydroxyl group from attack by the alkylene oxide compounds. This entire cumulative reaction has thus proven cumbersome, time-consuming, and costly. There thus exists a need to improve upon this procedure and potentially to produce a novel intermediate which ultimately provides the same ability of forming highly desirable oxyalkylenated xanthene colorants but does not require a multi-step process in forming the intermediate alone. The prior art has not accorded such an improvement within this specific area of colorant chemistry.

DESCRIPTION OF THE INVENTION

It is thus an object of the invention to provide a specific oxyalkylenated aminophenol intermediate for the production of an oxyalkylenated xanthene colorant. It is another object of this invention to provide a method of forming a specific propoxylated aminophenol intermediate which is a one-step process. A further object of the invention is to provide a specific propoxylated aminophenol intermediate which will not alternatively form a xanthene dyestuff upon reaction with phthalic anhydride and thus provides excellent yield of the desired colorant alone. Yet another object of this invention is to provide a relatively inexpensive method for producing such beneficial oxyalkylenated xanthene (or other type) colorants, the physical and chemical properties of which can be easily modified through subsequent reaction of the free hydroxyl groups with electrophiles such as anhydrides, isocyanates, esters, benzochlorides, and the like.

Accordingly, the present invention encompasses an aminophenol intermediate comprising at most a total of three moles of a constituent selected from the group of oxyalkylene groups having from 3 to 12 carbon atoms, alkoxy alkylester groups having from 3 to 12 carbon atoms, glycidol, and a glycidyl group wherein said constituent is solely bonded to the amine. The method of producing such a specific oxyalkylenated aminophenol intermediate is contemplated within this invention as well. The amine constituent may reside in any position relative to the phenol on the benzene ring (i.e., p-aminophenol, o-aminophenol, or m-aminophenol); however, aminophenol); however, m-aminophenol is preferred. Thus, the preferred m-aminophenol intermediate is also contemplated within this invention as is the method of making such a compound, as defined by the Formula (I)

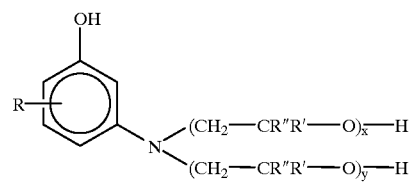

(I)

wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; and wherein R" is H or $CH_2R'$;

said method comprising the reaction of at most 3 moles of a compound selected from the group consisting of an alkylene oxide having from 3 to 10 carbon atoms and glycidol with a m-aminophenol compound of the Formula (II)

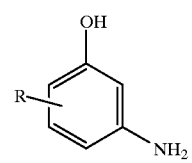

(II)

wherein R is selected from the group consisting of hydrogen, halo, $C_1$–$C_{20}$ alkoxy, and $C_1$–$C_{20}$ alkyl, a reaction temperature of from about 120 to about 250° F. The invention also covers the actual compound of Formula (I), above as well. Preferably R above (for both I and II) is hydrogen, $C_{1-4}$ alkoxy, or $C_{1-4}$ alkyl; most preferably R' is hydrogen. Also, preferably R" is methyl or ethyl (most preferably methyl), and R" is preferably H.

It has surprisingly been found that the aforementioned method produces the desired oxyalkylenated aminophenol compound without resulting in the formation of oxyalkylene groups on the phenolic hydroxyl group. The standard reactions followed in the past to attach oxyalkylene groups to amino or hydroxyl pendant groups have included reactions with ethylene oxide without any base present. The resultant reactions thus quickly drive the addition of the oxyalkylene groups to the undesired phenolic hydroxyl sites. In the inventive method, direct reaction with less reactive longer-chain alkylene oxides is utilized to effectuate the desired reaction without simultaneously driving the attack of longer-chain oxyalkylene groups to the phenolic hydroxyl moiety. Furthermore, the relatively low reaction temperature utilized (from about 120 to about 250° F.) also permits greater selectivity in the reaction of the longer-chain alkylene oxide by "slowing" the overall reaction. Comparative temperatures utilized for ethylene oxide additions are much higher (i.e., 280 to 320° F.). In turn, then, the ability to perform such a procedure in a one-step process translates into lower costs for the manufacturer of the ultimately produced colorant (i.e., xanthene-derivative colorants) as well as for the end-user of products colored with such compounds. Preferably, the reaction temperature utilized to form the intermediate ranges from about 150 to about 200° F. This range is optimum for the desired selectivity of the preferred propylene oxide reaction only with the amine hydrogens and not the phenolic hydroxyl group. The tower the temperature, theoretically the greater selectively, but cost-effectiveness is compromised as the reaction takes too long to accomplish. Higher temperatures (above 250°, preferably above 200°) speed up the reaction too much so as to result in the unwanted reaction between the propylene oxide and the phenolic hydroxyl group.

In order for this reaction to be successful, preferably from 2 to 3 motes of an alkylene oxide having from 3 to 10 carbon atoms (branched or unbranched and again, preferably propylene oxide) or glycidol in relation to the m-aminophenol starting material may be utilized. Greater molar amounts of the alkylene oxide will require inordinate and thus highly undesirable and costly amounts of time to produce the target oxypropylenated intermediate. Any amount below 1 mole will not provide sufficient propylene oxide to properly generate the desired oxypropylenated intermediate.

This reaction appears to work with any aminophenol compound, although highly preferred is a m-aminophenol compound conforming with the Formula (II)

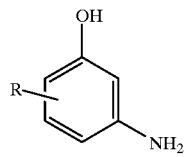

(II)

wherein R is selected from the group consisting of hydrogen, halo, $C_1$–$C_{20}$ alkoxy, and $C_1$–$C_{20}$ alkyl. Again, in each instance, the 1 to 3 moles of, for instance, propylene oxide (per m-aminophenol compound) when directly reacted with the starting aminophenol reactant at a suitable relatively low temperature, will only attack the amino groups, thereby Producing an oxypropyl-substituted aminophenol having at most an average of 1.5 monomers (i.e., 2 monomers on one site and 1 monomer on the other) of propylene oxide added per carbon-nitrogen bond of the amino moiety. The terms "directly reacted" or "direct reaction" regarding the longer-chain alkylene oxide reaction with the starting aminophenol is intended to mean a reaction including only those materials and no catalyst or water. Certain stabilizing compounds, such as methylimidazoles, and the like, and inert solvents, such as diglymne, and the like, may be present; however, the standard base catalysts and/or water is strictly avoided in this invention method to form the desired oxypropylated aminophenol intermediate.

The resultant intermediate of Formula (I) can then be reacted with at least one other reactant compound to form any number of different colorants. For instance, this intermediate may be reacted with phthalic anhydride (as discussed in U.S. Pat. No. 5,250,708, for example) to produce a xanthene-derivative compound. Alternatively, xanthene colorants may be formed through the reaction of at least 2 moles of the inventive intermediate with one note of a benzaldehyde (preferably one with carboxylic or sulfonate groups attached, such as benzaldehyde-2,4-disulfonic acid), as taught within the Barry, Jr. patent., as well as through the reaction of other compounds, such as, as merely an example, o-formyl-benzenesulfonic acid. The oxypropylene groups present on the nitrogens of the preferred xanthene derivative may then be reacted with other electrophilic and/or oxyalkylene groups in order to produce any polyoxyalkylenated xanthene colorant. This intermediate thus facilitates the production of any polyoxyalkylenated-xanthene colorant for use in any number of different media and/or on a myriad of substrates. Furthermore, the inventive intermediate will not alternatively form the correlative xanthene dyestuff during the reaction with phthalic anhydride. Such a dyestuff is highly regulated and poses potential toxicity problems and thus it is desirable to avoid production of such a compound. Furthermore, the dyestuff cannot be modified physically and/or chemically since there are no remaining reactive sites at which electrophilic groups may be attached. Because of the presence of oxypropylene groups, the phthalic anhydride only reacts with the phenolic hydroxyl group of the aminophenol, in turn forming the desired xanthene colorant and not the dyestuff. For example, U.S. Pat. No. 5,250,708 also teaches a method of producing a poly(oxyalkylene) xanthene colorant by reacting 2-(4-N,N-diethylamine-2-hydroxy benzoyl) benzoic acid with 3-methoxy-N,N-di (polyoxyalkylene oxide) aniline. The benzoic acid intermediate is produced in a reversible reaction from N,N-diethyl-m-aminophenol and phthalic anhydride. Since some residual diethyl-m-aminophenol may be present during this subsequent reaction, the intermediate may react with the N,N-diethyl-m-aminophenol to form the xanthene dyestuff. In the inventive method, such dyestuff formation is prevented since there is no use or production of N,N-diethyl-m-aminophenol. The inventive method and the inventive intermediate therefore provide clear distinct advantages over the previously disclosed xanthene compounds production methods.

Additionally, the inventive intermediate can be reacted with other reactant compounds to form other types of colorants. For example, an oxazine colorant may be formed by nitrosating one mole of the inventive intermediate and subsequently reacting that reactant compound with a second mole of the inventive intermediate. As with the xanthene colorants, above, the free hydroxyl groups may then be reacted with electrophilic or oxyalkylene groups to form different oxazine derivatives.

Furthermore, other colorants may also be formed, such as coumarins, through the reaction of the inventive intermediate with other reactant compounds such as, without limitation, ethylcyanoacetate and phenylenediamine. Upon production of the target coumarin, as with the aforementioned colorants, the free hydroxyl groups may then be subsequently reacted with electrophilic or oxyalkylene groups to form different coumarin derivatives.

DESCRIPTION OF THE PREFERRED EMBODIMENT

The preferred embodiments of this invention are provided below:

Intermediate Formation

The general method of making the preferred inventive intermediate is as follows:

EXAMPLE 1

140 parts of anisole (as a solvent) were charged into a reactor vessel with 350 parts of m-aminophenol. To this, 373 parts of propylene oxide (thus in a 2 mole to 1 mole ratio to the aminophenol reactant) were slowly added while maintaining a reaction temperature of about 150° F. and a pressure of from about 20 to about 60 psi. Upon completion of the propylene oxide addition, the reaction was maintained at its temperature and pressure for about 2 hours. After that time, the resultant mixture was removed from the reaction vessel. The anisole was removed by the azeotrope with water to yield a propoxylated m-aminophenol having an average of about 1 mole of propylene oxide per carbon-amino bond on the amino linkage. The structure was confirmed by analysis with electron spray mass spectroscopy and is represented by Formula (III) where x and y are both an average of about 1:

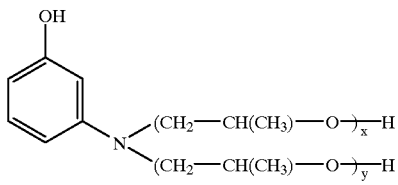

(III)

EXAMPLE 2

400 parts of diglymne (as a solvent) were charged into a reactor vessel with 957 parts of m-aminophenol. The mixture was heated with stirring to 150° F. and 1400 g of propylene oxide (a 2.75 to 1 mole ratio relative to the m-aminophenol reactant) was slowly added over 41.25 hours while maintaining a pressure of about 60 psi. The reaction mixture was heated at 150° F. for 5 hours after all of the propylene oxide had been added. After completion of the reaction, the reaction mixture was stripped for 15 minutes at 150° F. to remove any unreacted propylene oxide is and the product was removed from the reactor vessel.

To determine the amount of propylene oxide substitution, a sample of the product was reacted with excess acetic anhydride. The reaction product was washed three times with water and residual water removed on a rotary evaporator. NMR integration of the acetylated product showed an average of 2.7 moles of propylene oxide with no propylene oxide substitution of the phenolic hydroxide. The produced intermediate is represented by Formula (IV) where x and y are both an average of about 1.5:

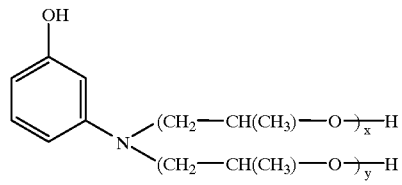

(IV)

Colorant Formation

The general methods of making the preferred inventive colorants are as follows:

EXAMPLE 3 (Xanthene)

22.5 parts of N,N-dipropoxylated m-aminophenol was charged into a flask containing 50 parts of anisole. To this mixture was charged 44.4 parts of phthalic anhydride and 0.7 parts of 1-methylimidazole. The reactants were then heated up to 100° C. and maintained at a temperature from about 100 to 105° C., until the 340 nm peak, representing the inventive intermediate, in the uv/vis spectrum has disappeared (through measurement by a uv/vis spectrophotometer). Ant that time, 22.5 parts of N,N-dipropoxylated m-aminophenol was then added to the reaction followed by another 20 parts of anisole and 15.3 parts of phosphorus oxychloride. The resultant mixture was then heated to about 155° C. and maintained at a temperature from about 155 to about 160° C. for 2 hours or until the 340 mn peak again disappeared and the peak at 550 nm, representing the xanthene target colorant, ceases growing. At that time, the resultant product was neutralized and the anisole was removed by the azeotrope with water out of the reaction to yield N,N-dipropoxylated xanthene (exhibiting a brilliant magenta hue), represented by Formula (V) wherein X⁻ is chloride ion:

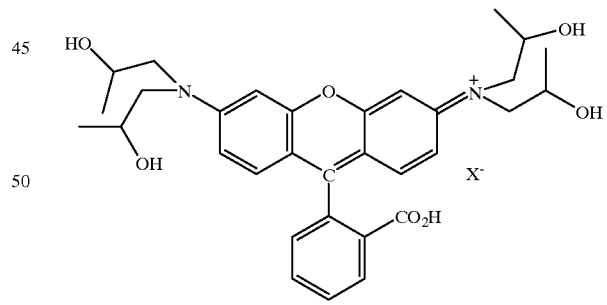

(V)

EXAMPLE 4 (Oxazine)

22.5 parts of N,N-dipropoxylated m-aminophenol was charged into a reactor followed with 37.5 parts of water and 1.5 parts of 2-ethylhexanol. To this mixture was added 20 parts of 37% HCl. The resultant mixture was cooled to 0–5° C. In a separate vessel, 73 parts of sodium nitrite was dissolved in 12.5 parts of water and subsequently added to the cooled mixture (at a temperature from 0 to 5° C.). This mixture was stirred for about 1 hour. This reaction formed a nitroso derivative of the inventive intermediate.

Separately, 22.5 parts of N,N-dipropoxylated m-aminophenol was charged to a flask and ethanol was added until 500 mL of this mixture was obtained and brought to a reflux. The nitroso derivative was then added to the refluxing mixture in three equal portions of about 167 mL each, with 10 minute intervals between introductions. The entire mixture was allowed to reflux for 4 hours and then cooled to room temperature overnight (about 14 hours). At that time, the ethanol was evaporated to yield a an oxypropylene oxazine colorant exhibiting a brilliant blue hue and represented by Formula (VI) wherein $X^-$ is chloride ion:

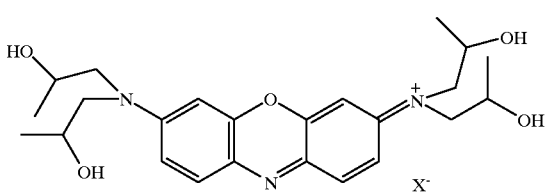

(VI)

EXAMPLE 5 (Coumarin)

This colorant was produced in three distinct steps, outlined below:

A. Preparation of N,N-dipropoxy-m-aminophenol diacetate 22.5 parts of N,N-dipropoxy-m-aminophenol were charged to a reactor vessel followed by 22.0 parts of-acetic anhydride and 0.5 parts of 1-methylimidazole. The mixture was then heated to about 130 to 140° C. and held for 3 hours. The acetic acid and excess anhydride were then distilled out at a temperature from 130 to 140° C. leaving the N,N-dipropoxy-m-aminophenol diacetate product.

B. Preparation of p-formyl-N,N-dipropoxy-m-aminophenol 27.7 parts of dimethylformamide were charged to a reaction flask and cooled to about 0 to 5° C. To this was then slowly added 20.7 parts of phosphorus oxychloride while maintaining the same low temperature. 31.1 parts of N,N-dipropoxy-m-aminophenol diacetate were then charged to a separate reactor vessel and to which the complex of dimethylformamide and phosphorus oxychloride was then added while maintaining the temperature between 5 and 10° C.

Upon completion of the addition of the complex, the resultant mixture was heated to about 85° C. and maintained at that temperature for about 2 hours. The mixture was then cooled and neutralized with 50% by weight of sodium hydroxide. The pH was then adjusted to about 12.5 through the introduction of 80 parts water, 21.5 parts 50% NAOH, and 4.7 parts of 45% KOH. This resultant composition was then heated to about 100° C. for 2 hours after which the excess base was neutralized with sulfuric acid, thereby obtaining p-formyl-N,N-dipropoxy-m-aminophenol.

C. Preparation of the Coumarin Colorant 100 parts of 50% sulfuric acid were charged to a reactor vessel to which 10.8 parts of o-phenylenediamine and 11.4 parts of ethylcyanoacetate were then subsequently added. This mixture was heated to a reflux until all of the o-phenylenediamine disappeared from the system. To this mixture was then added 25.4 parts of the p-formyl-N,N-dipropoxy-m-aminophenol produced in parts B above and the resultant composition was maintained at a temperature of about 90–95° C. for 1 hour. Hydrolysis with aqueous NAOH resulted in a bright yellow coumarin colorant represented by Formula (VII):

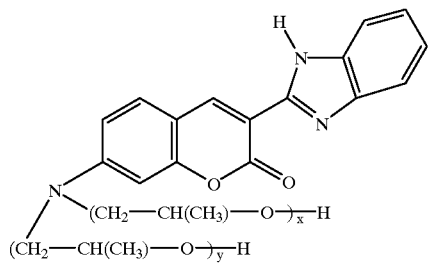

(VII)

There are, of course, many alternative embodiments and modifications of the present invention which are intended to be included within the spirit and scope of the following claims.

What we claim is:

1. An aminophenol intermediate comprising at most a total of three moles of a constituent selected from the group of oxyalkylenes having from 3 to 12 carbon atoms, alkoxyalkylesters having from 3 to 12 carbon atoms, glycidol, and a glycidyl group wherein said constituent is solely bonded to the amine.

2. The intermediate of claim 1 further defined by the Formula (I)

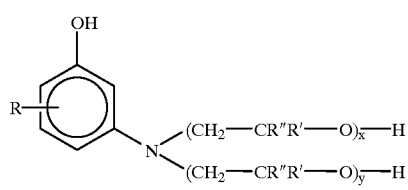

(I)

wherein x and y are the same or different and are 0, 1, or 2, and wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; and wherein R" is H or $CH_2R'$.

3. The compound of claim 1 wherein x and y are both 1; R is selected from the group consisting of hydrogen, $C_1$–$C_4$ alkoxy, and $C_1$–$C_4$ alkyl; R' is selected from methyl and ethyl; and R" is H.

4. The compound of claim 3 wherein R is hydrogen and R' is methyl.

5. A method of making an aminophenol intermediate comprising the steps of providing an aminophenol compound and directly reacting to said aminophenol at most three moles of a constituent selected from the group consisting of alkylene oxide containing having from 3 to 12 carbon atoms, glycidol, and a glycidyl group.

6. The method of claim 5 wherein said aminophenol inter-mediate is further defined by the Formula (I)

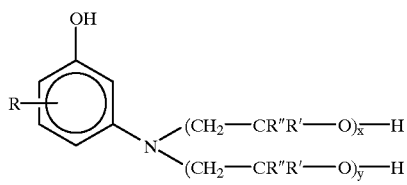

(I)

wherein x and y are the same or different and are 0, 1, or 2, and wherein x+y is greater than 0 and less than 4; wherein R is selected from the group consisting of hydrogen, halo, formyl, $C_1$–$C_{20}$ alkoxy, and $C_1$–$C_{20}$ alkyl; wherein R' is selected from the group consisting of $C_1$–$C_{10}$ alkoxy, $C_1$–$C_{10}$ polyoxyalkoxy, $C_1$–$C_{10}$ alkylester, and $C_1$–$C_{10}$ alkyl; and wherein R" is H or $CH_2R'$; and wherein said aminophenol is further defined by the Formula (II)

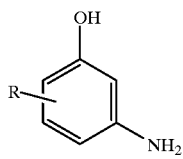

(II)

wherein R is selected from the group consisting of hydrogen, halo, $C_1$–$C_{20}$ alkoxy, and $C_1$–$C_{20}$ alkyl.

7. The method of claim 5 wherein the direct reaction is performed at a reaction temperature of from about 120 to about 250° F.

8. The method of claim 6 wherein x and y are both 1; wherein R is selected from the group consisting of hydrogen, $C_1$–$C_4$ alkoxy, and $C_1$–$C_4$ alkyl; wherein R' is selected from the group consisting methyl and ethyl; and wherein R" is H.

9. The method of claim 8 wherein R is hydrogen and wherein R' is methyl.

10. The method of claim 9 wherein the reaction temperature is about 150 to about 200° F.

11. A xanthene colorant produced through the reaction of the intermediate of claim 2 and at least one other reactant compound selected from the group consisting of a phthalic anhydride and a benzaldehyde.

12. The xanthene colorant of claim 11 wherein said at least one other reactant compound is phthalic anhydride.

13. An oxazine colorant produced through the reaction of the intermediate of claim 2 and a nitrosated derivative of said intermediate.

14. A coumarin colorant produced through the reaction of the intermediate of claim 2 and ethylcyanoacetate.

15. A coumarin colorant produced through the reaction of the intermediate of claim 2 and both an ethylcyanoacetate and a phenylenediamine.

* * * * *